(12) United States Patent
Adams et al.

(10) Patent No.: US 7,713,262 B2
(45) Date of Patent: May 11, 2010

(54) DISPOSABLE INFUSION DEVICE WITH LINEAR PERISTALTIC PUMP

(75) Inventors: John M. Adams, Sammamish, WA (US); Clifton A. Alferness, Port Orchard, WA (US); Daniel Hawkins, Newcastle, WA (US)

(73) Assignee: Calibra Medical, Inc., Redwood City, CA (US)

( * ) Notice: Subject to any disclaimer, the term of this patent is extended or adjusted under 35 U.S.C. 154(b) by 188 days.

(21) Appl. No.: 11/516,456

(22) Filed: Sep. 6, 2006

(65) Prior Publication Data

US 2008/0097324 A1 Apr. 24, 2008

Related U.S. Application Data

(60) Provisional application No. 60/809,957, filed on May 31, 2006.

(51) Int. Cl.
*A61K 9/22* (2006.01)
(52) U.S. Cl. .................................... 604/890.1
(58) Field of Classification Search ............. 604/890.1, 604/65, 66, 67, 184, 185, 151, 152, 154, 604/228, 134, 135, 143
See application file for complete search history.

(56) References Cited

U.S. PATENT DOCUMENTS

| | | | | |
|---|---|---|---|---|
| 5,165,874 | A | * | 11/1992 | Sancoff et al. .............. 417/474 |
| 5,167,631 | A | | 12/1992 | Thompson et al. |
| 5,858,001 | A | * | 1/1999 | Tsals et al. .................. 604/135 |
| 6,251,098 | B1 | | 6/2001 | Rake et al. |
| 2003/0233069 | A1 | | 12/2003 | Gillespie, Jr. et al. |
| 2004/0193090 | A1 | * | 9/2004 | Lebel et al. ..................... 604/1 |
| 2005/0075607 | A1 | * | 4/2005 | Lee ............................. 604/131 |

OTHER PUBLICATIONS

Lucchesi, PCT International Search Report, Jul. 2, 2008.
Lucchesi, PCT International Search Report, Sep. 11, 2008.

* cited by examiner

*Primary Examiner*—Nicholas D Lucchesi
*Assistant Examiner*—Christopher D Koharski
(74) *Attorney, Agent, or Firm*—Richard O. Gray, Jr.; Graybeal Jackson LLP

(57) ABSTRACT

A wearable infusion device delivers a liquid medicant, such as insulin, to a patient. The infusion device comprises a base that contacts a patient's skin and a reservoir arranged to contain a liquid medicant to be delivered beneath a patient's skin. The reservoir has an outlet through which the medicant flows. The infusion device further includes a flexible conduit communicating with the outlet of the reservoir and a pump that causes the medicant to flow down the conduit.

39 Claims, 5 Drawing Sheets

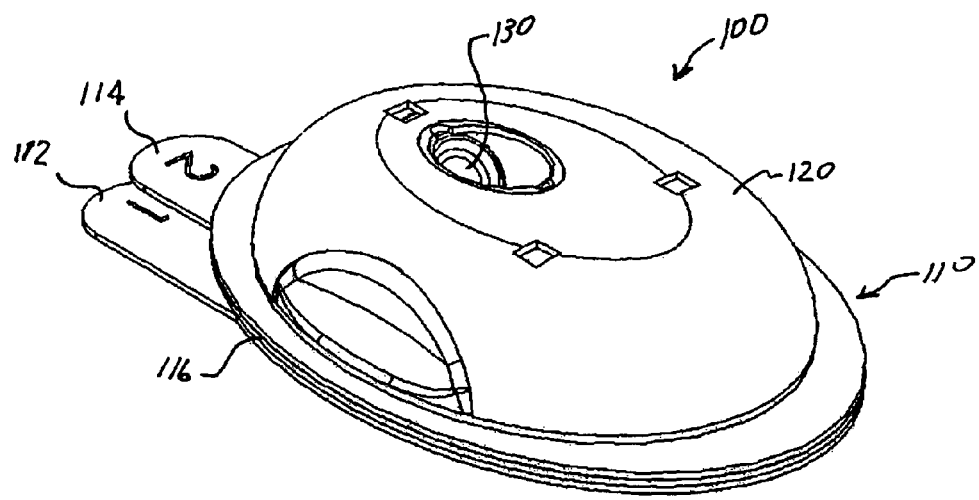
FIG. 1
FIG. 2
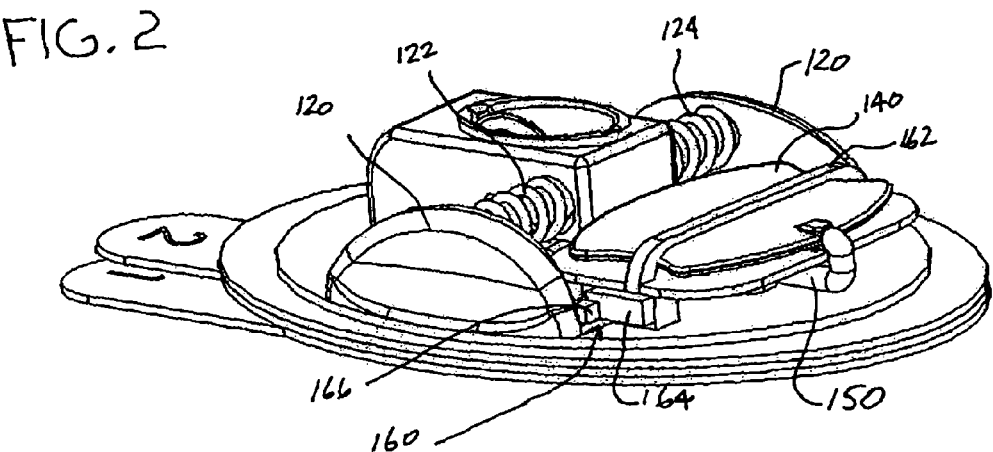

DISPOSABLE INFUSION DEVICE WITH LINEAR PERISTALTIC PUMP

CLAIM OF PRIORITY

This application claims priority to U.S. Provisional Application Ser. No. 60/809,957, filed on May 31, 2006, which is incorporated by reference.

BACKGROUND OF THE INVENTION

Tight control over the delivery of insulin in both type I diabetes (usually juvenile onset) and type II diabetes (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses for meals and snacks. These infusion systems have shown to improve control of blood glucose levels, however, they suffer the drawbacks of size, cost, and complexity, which prevents many patients from accepting this technology over the standard subcutaneous injections. These pumps are electronically controlled and must be programmed to supply the desired amounts of basal and bolus insulin.

Hence, there is a need in the art for a simple, mechanically driven infusion device for both basal needs and boluses that is directly attached to the body and does not require any electronics to program the delivery rates. The insulin is preferably delivered through a small, thin-walled tubing (cannula) through the skin into the subcutaneous tissue similar to technologies in the prior art. The present invention, in its various embodiments, is directed to providing such a device.

SUMMARY OF THE INVENTION

The invention provides a wearable infusion device comprising a base that contacts a patient's skin and a reservoir arranged to contain a liquid medicant to be delivered beneath a patient's skin. The reservoir has an outlet through which the medicant flows. The device further comprises a flexible conduit communicating with the outlet of the reservoir and a pump that causes the medicant to flow down the conduit.

The pump is arranged to act upon the conduit to cause the medicant to flow. The device may further comprise a valve upstream from the pump that seals off the conduit from the reservoir as the pump acts upon the conduit. The pump may be a peristaltic pump comprising a linear peristaltic pump.

The device may further comprise a pair of opposed actuator buttons coupled to the pump which, when concurrently pressed, cause the pump to act upon the conduit to cause the medicant to flow down the conduit.

The device may further comprise a spring associated with each of the actuator buttons that bias the actuating buttons into a starting position. The pump may comprise at least one pressure member that applies pressure to the conduit, and the at least one pressure member may be integrally formed with one of the actuator buttons. The pump may comprise a pair of pressure members that apply pressure to opposite sides of the conduit. Each pressure member may be integrally formed with one of the actuator buttons. The pressure members are preferably elongated and disposed on opposite sides of the conduit. The pressure members may, for example, be spaced apart from the conduit on opposite sides of the conduit and be progressively more closely spaced in the direction of the reservoir.

The device may further comprise a check valve downstream from the pump that precludes backflow of the medicant. The device may further comprise an actuator that actuates the pump, and the check valve may be arranged to close in response to the actuator. The check valve may be coupled to the actuator. The check valve downstream from the pump may close the conduit after the pump causes the fluid medicant to flow to preclude medicant from dripping from the reservoir.

In another embodiment, the invention provides a wearable infusion device comprising a base that contacts a patient's skin, a reservoir arranged to contain a liquid medicant to be delivered beneath a patient's skin, and having an outlet through which the medicant flows, and a flexible conduit communicating with the outlet of the reservoir. The device further comprises a peristaltic pump that acts upon the conduit to cause the medicant to flow down the conduit, and a pair of actuator buttons, which, when concurrently pressed, cause the peristaltic pump to act upon the conduit.

The device may further comprise a check valve downstream from the peristaltic pump that precludes backflow of the medicant. The check valve may be coupled to at least one of the actuator buttons. The peristaltic pump may comprise a pair of pressure members disposed on opposite sides of the conduit. The pressure members may be elongated, spaced apart from the conduit on opposite sides of the conduit, and progressively more closely spaced in the direction of the reservoir. Each pressure member may be plastic and formed as one-piece with an associated one of the actuator buttons. The device may further comprise a spring associated with each of the actuator buttons for biasing the actuating buttons into a starting position.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 1 is a perspective view of an infusion device embodying the present invention;

FIG. 2 is a perspective view of the device of FIG. 1 with its top cover removed and in a condition ready for having its reservoir filled with liquid medicant;

DETAILED DESCRIPTION OF THE INVENTION

Figure 3:
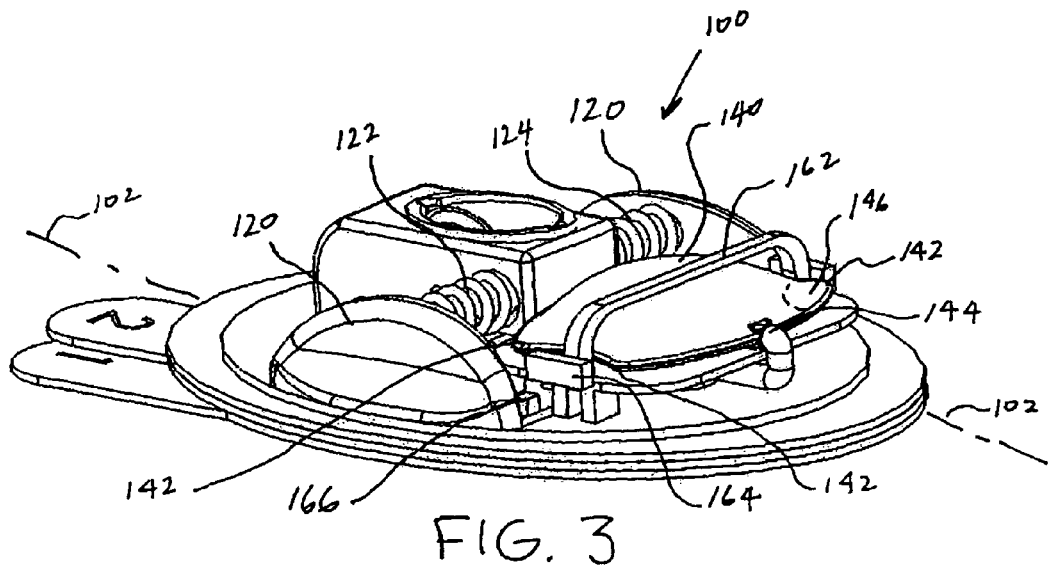
FIG. 3 is a perspective view of the infusion device of FIG. 1 with its top cover removed after its reservoir has been filled with liquid medicant.

Referring now to FIG. 1, it illustrates an infusion device 100 embodying the present invention. The infusion device 100 may be useful, for example, in providing boluses of a liquid medicant, such as insulin, to be delivered beneath a patient's skin.

The device 100 generally includes a base 110, a top cover 120, and a cannula port 130. The base 110 prior to application to the patient's skin, carries a first tab member 112 and a second tab member 114. The first tab member 112, when removed, exposes a layer 116 of antiseptic material such as alcohol which may be rubbed against the skin of the patient in the area in which the device 100 is to be adhered. Once the antiseptic has been applied to the patient's skin, the second tab 114 is removed exposing an adhesive layer on the base 110 which is then used to adhere the device to the skin of the patient. Once the device is adhered to the skin of the patient, a cannula may be introduced into the device and beneath the skin of a patient through the cannula port 130.

As may be seen in FIG. 2, the device 100 further includes a pair of actuator push buttons 120 and a reservoir 140 arranged to contain the liquid medicant. As will be seen hereinafter, concurrent pressing of the actuator push buttons 120 causes the liquid medicant within the reservoir 140 to flow down a flexible conduit 150 and eventually beneath the skin of a patient. Each of the push buttons 120 are spring loaded by an associated spring 122 and 124 which return the push buttons 120 to their starting positions.

The reservoir 140 as shown in FIG. 2 does not yet contain the liquid medicant. A latch mechanism 160 precludes the push buttons 120 from being pressed when the reservoir 140 is empty. To that end, it will be noted that a follower bar 162 extends across the reservoir 140 and terminates at a latch member 164. A dog 166 is coupled to the push buttons 120 and engages the latch member 164 to preclude the actuator buttons 120 from being pushed when the reservoir is empty.

Referring now to FIG. 3, when the reservoir is filled as illustrated in FIG. 3, the follower bar 162 follows the expansion of the reservoir 140. To that end, the reservoir 140 is preferably formed of flexible material, such as plastic, and will expand upon being filled. The follower bar 162 follows the filling of the reservoir 140 to raise the latch member 164. When the reservoir is full, the latch member 164 is raised to such an extent that the dog 166 may pass thereunder to permit the push buttons 120 to be pressed to cause pumping of the liquid medicant to the patient. Again, the springs 122 and 124 assist in returning the push buttons 122 to a starting position.

The reservoir 140, as may be noted in FIG. 3, includes a plurality of raised portions 142 formed along its perimeter. This reservoir shape causes air pockets to be formed within the reservoir that traps air isolated from the reservoir outlet 144. Accordingly, the device 100 is intended to be worn with its major axis 102 horizontal. In such an orientation, air within the reservoir 140 may be trapped in the air pockets, such as air pocket 146.

Figure 4:
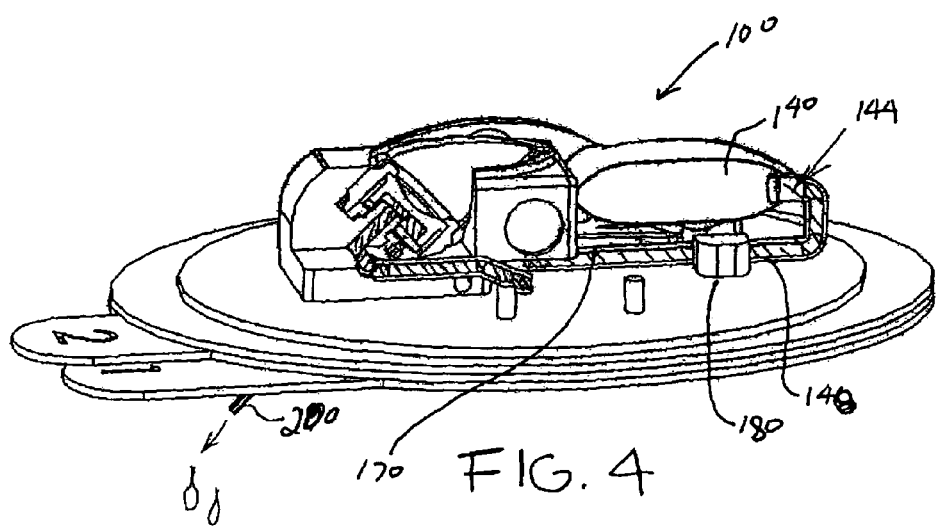
FIG. 4 is perspective view with portions cut away of the infusion device of FIG. 1 illustrating the path of the liquid medicant within the device.

Referring now to FIG. 4, it illustrates the fluid flow path of the liquid medicant upon being pumped responsive to the pressing of the actuator buttons 120. The fluid flow path is shown in dashed lines in FIG. 4. As maybe noted, the fluid flow from reservoir 140 begins at the outlet 144 along a flexible conduit 148. The fluid medicant is propelled by a pump, such as a linear peristaltic pump 170 to be described hereinafter. It first flows through a valve 180 which may be provided to isolate the pump 170 from the reservoir 140 when the pump 170 pumps the fluid medicant. The valve 180, under some circumstances, is optional, as for example when a linear peristaltic pump of the type described herein is employed as will be fully described hereinafter.

The fluid continues to flow along the flexible conduit 148 to eventually arrive at the cannula 200. It is then delivered to the patient beneath the patient's skin.

Figure 5:
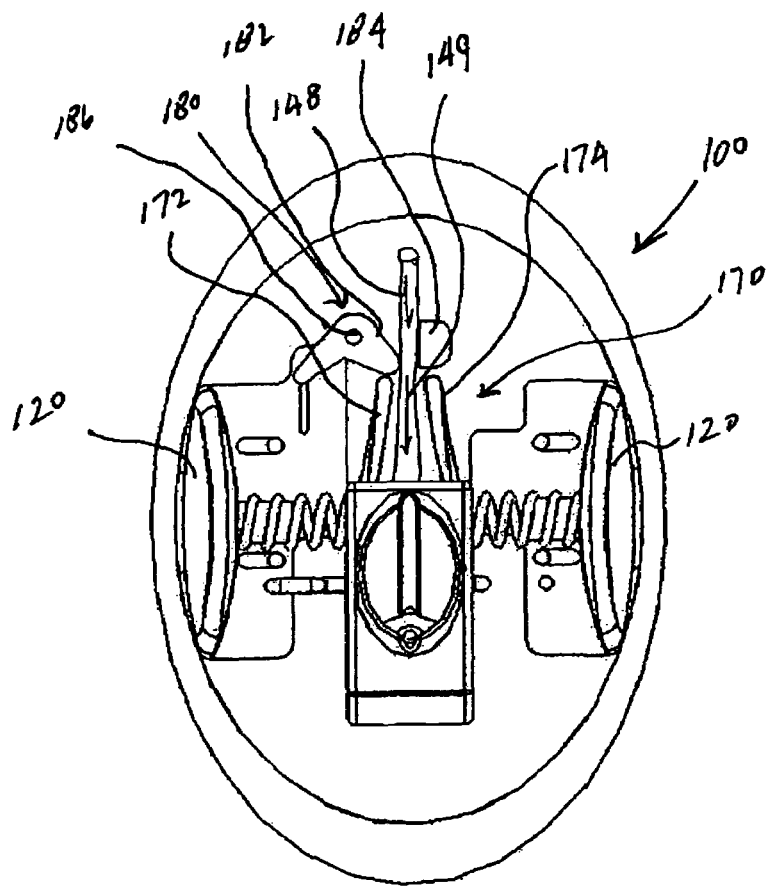
FIG. 5 is a top view of the device of FIG. 1 with its reservoir removed to illustrate the manner in which the liquid medicant is caused to flow within the device.
Figure 6:
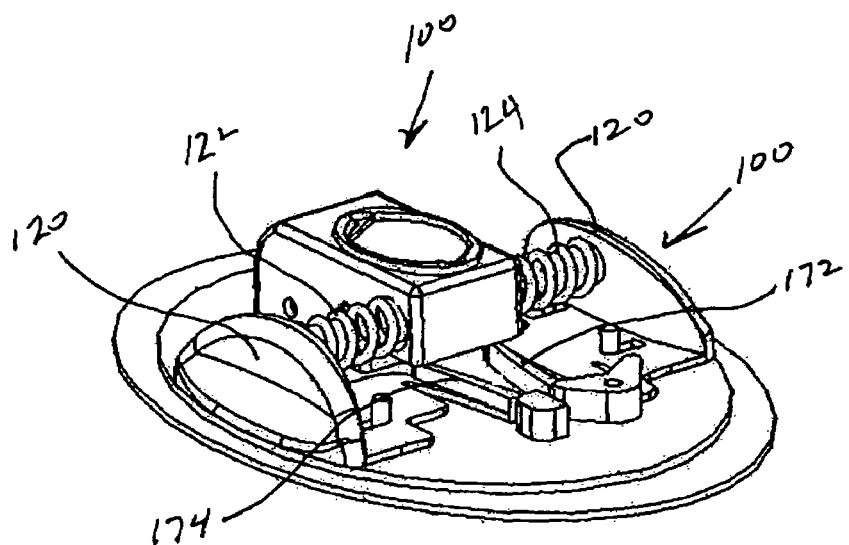
FIG. 6 is a perspective view of the infusion device of FIG. 1 with its reservoir removed illustrating further aspects of the pump thereof.

FIGS. 5 and 6 show the peristaltic pump of the device 100 in greater detail. Here it may be seen that the peristaltic pump comprises a pair of pressure members 172 and 174. The pressure members 172 and 174 are disposed on opposite sides of the flexible conduit 148. The direction of fluid flow is indicated by the arrows 149 in a direction away from the reservoir (not shown). The pressure members 172 and 174 are spaced apart such that they become increasingly closer together in an upstream direction with respect to the fluid flow. Hence, when the pressure members 172 and 174 act upon the flexible conduit 148, they will serve to first pinch the flexible conduit closed and then, upon exerting additional pressure, squeeze the conduit to force the liquid medicant in the downstream direction.

As previously mentioned, the valve 180 is optional. If the pump utilized is not a pump as illustrated herein that first closes off the conduit, the valve 180 may be coupled to the actuator buttons 120 so that the valve 180 closes the conduit 148 before pressure is exerted on the flexible conduit 148 by the pump. To that end, the valve 180 includes a first valve member 182 and a second stationary valve member 184. Valve member 182 pivots about pivot point 186 upon the pressing of the actuator buttons 120 to pinch the flexible conduit closed against the stationary member 184.

In FIG. 6, it may be more clearly seen that each pressure member 172 and 174 is integrally formed with an associated one of the actuator buttons 120. More specifically, each pressure member may be formed as one piece with its actuator button 120. Because the device 100 is intended to be disposable, the actuator buttons and hence the pressure members 172 and 174 may be formed of plastic.

Once the actuator buttons 120 are pressed and the peristaltic pump 170 causes the liquid medicant to flow down the flexible conduit 148, the actuator buttons 120 are returned to their starting positions by their respective springs 122 and 124. At this point in time, the flexible conduit 148 is charged with fluid to cause the fluid medicant to exit the cannula 190 as illustrated in FIG. 4. To guard against back pressure within the cannula 190 and flexible conduit which would otherwise lessen the amount of liquid medicant received by the patient, a check valve 190 is provided. The check valve 190 is downstream from the pump 170 and performs at least two functions. Firstly, the check valve 190 when closed precludes back flow of the medicant and assures that the medicant within the flexible conduit from the check valve to the cannula 200 is eventually diffused into the patient. It also precludes unintended leaking of the liquid medicant into the patient in between actuations of the push buttons 120.

Figure 7:
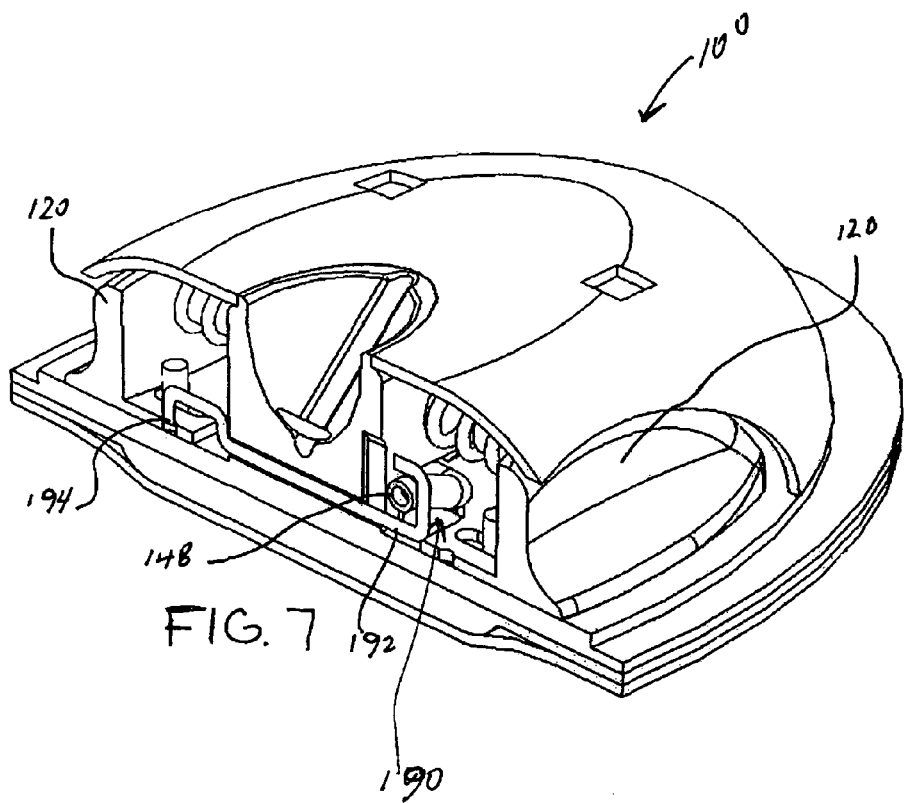
FIG. 7 is a perspective view of the infusion device of FIG. 1 with portions cut away to illustrate a safety check valve in its opened position.
Figure 8:
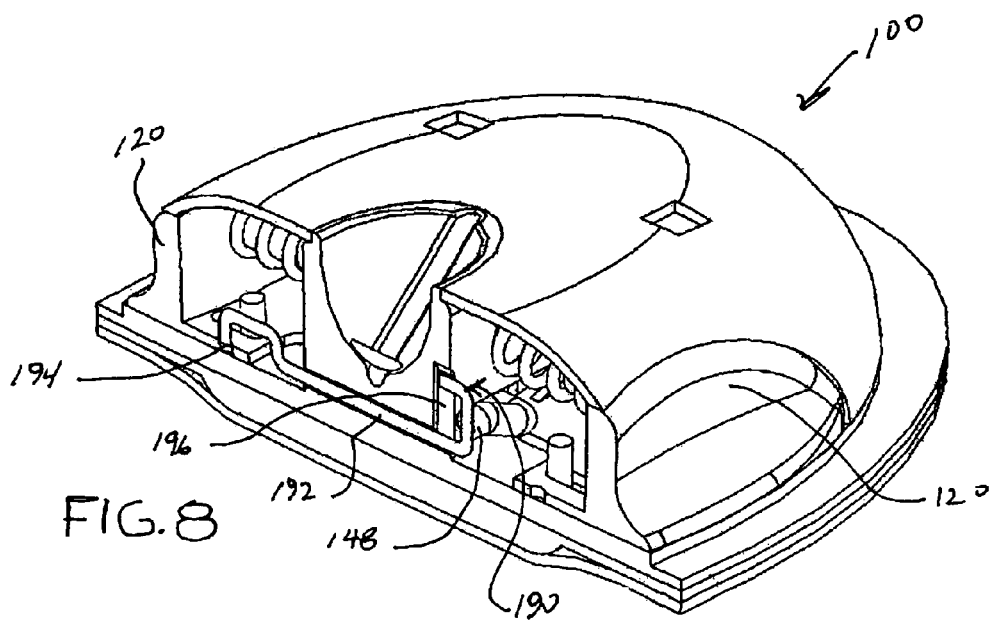
FIG. 8 is a perspective view similar to FIG. 7 illustrating the safety check valve closed.

With particular reference to FIGS. 7 and 8, in FIG. 7, it will be noted that the valve 190 is formed by a closing member 192 which is coupled to an actuator push button 120 at an attachment point 194. When the actuator buttons 120 are concurrently pressed, the closure member 192 slides to the position indicated in FIG. 7 to an opened position to permit fluid flow through the flexible conduit 148. As may be seen in FIG. 8, when the actuator buttons 120 are released, the closure member 192 is caused to move in a direction towards the flexible conduit 148 and eventually pinches the flexible conduit 148 closed between the closure member 192 and a stationary wall 196. Once the valve 190 is closed as shown in FIG. 8, liquid medicant will not be permitted to inadvertently drip from the reservoir, flow through the conduit, and be delivered to the patient.

Figure 9:
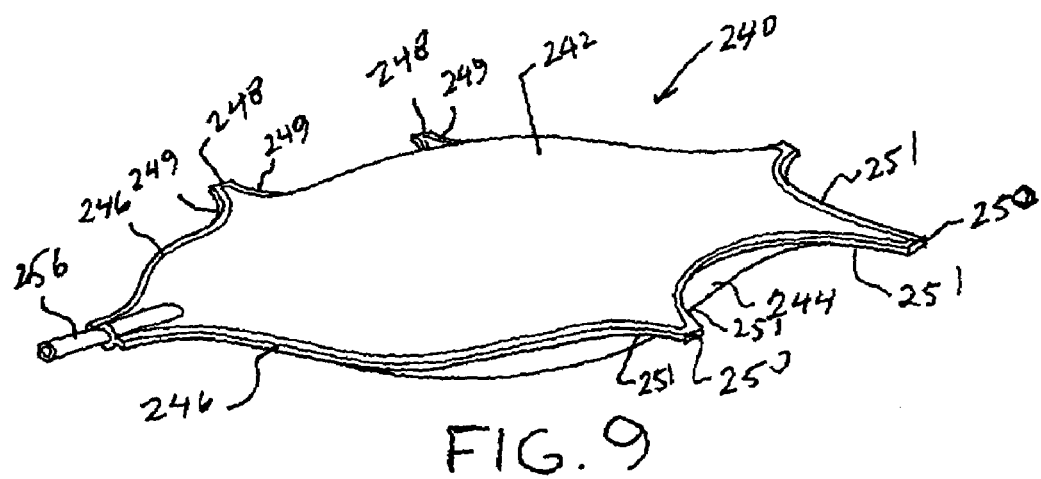
FIG. 9 is a perspective view of a reservoir which may be used in the infusion device of FIG. 1 in accordance with an alternate embodiment.
Figure 10:
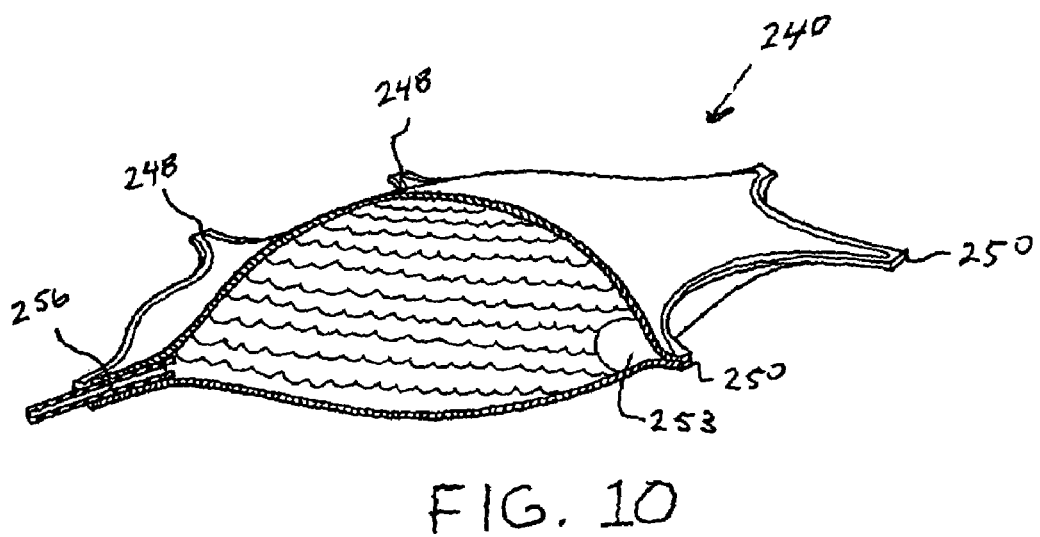
FIG. 10 is a perspective view with portions cut away of the reservoir of FIG. 9 illustrating further aspects thereof according to the invention.

Referring now to FIGS. 9 and 10, they show an alternative flexible reservoir which may be used in the infusion pump according to the invention. The flexible reservoir 240 is formed of flexible sheet material including a sheet 242 and a sheet 244. The sheet materials 242 and 244 are sealed along a peripheral seal line 246. As may be clearly noted in FIGS. 9 and 10, the reservoir 240 is shaped to form raised portions 248 on one side of the reservoir and raised portions 250 on the opposite side of the reservoir. The raised portions 248 and 250 may be pointed regions having concave sidewalls. For example, pointed regions 248 have concave sidewalls 249 and pointed regions 250 have concave sidewalls 251.

When the reservoir 240 is deployed in an infusion device, such as infusion device 100 of FIG. 1, it may be disposed so that the raised regions 250 and 248 are along a pane having a substantially vertical component. With the reservoir 240 being disposed such that the raised regions 250 are above the raised regions 248, air pockets, such as air pocket 253 will be formed within the reservoir 240. The air pocket 253 is isolated from the outlet 256 to assure that no air will become entrapped in the liquid medicant being delivered to the patient.

Hence, as may be seen from the foregoing, the present invention provides a simple, mechanically driven infusion device that provides boluses of liquid medicant, such as insulin, and which may directly attached to the body of a patient. The device does not require any electronics to deliver or program the delivery of the medicant. The liquid medicant, such as insulin, may be delivered through a small cannula into the subcutaneous tissue of the patient as is common in the art.

While particular embodiments of the present invention have been shown and described, modifications may be made, and it is therefore intended in the appended claims to cover all such changes and modifications which fall within the true spirit and scope of the invention as defined by those claims.

What is claimed:

1. A wearable infusion device comprising: a base that contacts a patient's skin;
   a reservoir arranged to contain a liquid medicant to be delivered beneath a patient's skin, the reservoir having an outlet through which the medicant flows;
   a flexible conduit communicating with the outlet of the reservoir, the conduit being configured to be compressed by at least one pressure member; and
   a pump comprising at least one pressure member that applies pressure to the conduit to cause the medicant to flow down the conduit, and
   a pair of opposed actuator buttons coupled to the pump which, when concurrently pressed, cause the pump to act upon the conduit to cause the medicant to flow down the conduit.

2. The device of claim 1, wherein the pump acts upon the conduit to cause the medicant to flow.

3. The device of claim 2, further comprising a valve upstream from the pump that seals off the conduit from the reservoir as the pump acts upon the conduit.

4. The device of claim 2, wherein the pump is a peristaltic pump.

5. The device of claim 4, wherein the peristaltic pump comprises a linear peristaltic pump.

6. The device of claim 1, further comprising a spring associated with each of the actuator buttons that bias the actuating buttons into a starting position.

7. The device of claim 1, wherein the at least one pressure member is integrally formed with one of the actuator buttons.

8. The device of claim 1, wherein the pump comprises a pair of pressure members that apply pressure to opposite sides of the conduit, and wherein each pressure member is integrally formed with one of the actuator buttons.

9. The device of claim 8, wherein the pressure members are elongated and disposed on opposite sides of the conduit.

10. The device of claim 1, further comprising a check valve downstream from the pump that precludes backflow of the medicant.

11. The device of claim 10, further comprising an actuator that actuates the pump, and wherein the check valve closes in response to the actuator.

12. The device of claim 11, wherein the check valve is coupled to the actuator.

13. The device of claim 11, wherein the check valve is coupled to the actuator.

14. The device of claim 1, further comprising a check valve downstream from the pump that closes the conduit after the pump causes the fluid medicant to flow to preclude medicant from dripping from the reservoir.

15. The device of claim 14, further comprising an actuator that actuates the pump, and wherein the check valve closes in response to the actuator returning to a start position.

16. A wearable infusion device comprising:
   a base that contact a patient's skin;
   a reservoir arranged to contain a liquid medicant to be delivered beneath a patient's skin, the reservoir having an outlet through which the medicant flows;
   a flexible conduit communicating with the outlet of the reservoir;
   a pump that causes the medicant to flow down the conduit; and
   a pair of opposed actuator buttons coupled to the pump which, when concurrently pressed, cause the pump to act upon the conduit to cause the medicant to flow down the conduit,
   wherein the pump comprise a pair of pressure members that apply pressure to opposite sides of the conduit,
   wherein each pressure member is integrally formed with one of the actuator buttons,
   wherein the pressure members are elongated and disposed on opposite sides of the conduit, and
   wherein the pressure members are spaced apart from the conduit on opposite sides of the conduit and are progressively more closely spaced in the direction of the reservoir.

17. The device of claim 16, wherein each pressure member and its associated actuator button are formed of one-piece plastic.

18. A wearable infusion device comprising:
   a base that contacts a patient's skin;
   a reservoir arranged to contain a liquid medicant to be delivered beneath a patient's skin, the reservoir having an outlet through which the medicant flows;
   a flexible conduit communicating with the outlet of the reservoir the flexible conduit being configured to be compressed by at least one pressure member;

a peristaltic pump comprising at least one pressure member that acts upon the conduit to cause the medicant to flow down the conduit; and a pair of actuator buttons, which, when concurrently pressed, cause the peristaltic pump to act upon the conduit.

19. The device of claim 18, further comprising a check valve downstream from the peristaltic pump that precludes backflow of the medicant.

20. The device of claim 19, wherein the check valve is coupled to at least one of the actuator buttons.

21. The device of claim 18, wherein the peristaltic pump comprises a pair of pressure members disposed on opposite sides of the conduit.

22. The device of claim 21, wherein each pressure member of the pump is integrally formed with one of the actuator buttons.

23. The device of claim 18, further comprising a spring associated with each of the actuator buttons for biasing the actuating buttons into a starting position.

24. A wearable infusion device comprising:
a base that contact a patient's skin;
a reservoir arranged to contain a liquid medicant to be delivered beneath a patient's skin, the reservoir having an outlet through which the medicant flows;
a flexible conduit communicating with the outlet of the reservoir;
a peristaltic pump that acts upon the conduit to cause the medicant to flow down the conduit; and
a pair of actuator buttons, which, when concurrently pressed, cause the peristaltic pump to act upon the conduit,
wherein the peristaltic pump comprises a pair of pressure members disposed on opposite sides of the conduit, and
wherein the pressure members are elongated, spaced apart from the conduit on opposite sides of the conduit, and are progressively more closely spaced in the direction of the reservoir.

25. A wearable infusion device comprising:
a base that contacts a patient's skin;
a reservoir arranged to contain a liquid medicant to be delivered beneath a patient's skin, the reservoir having an outlet through which the medicant flows;
a flexible conduit communicating with the outlet of the reservoir;
a peristaltic pump that acts upon the conduit to cause the medicant to flow down the conduit; and
a pair of actuator buttons, which, when concurrently pressed, cause the peristaltic pump to act upon the conduit,
wherein the peristaltic pump comprises a pair of pressure members disposed on opposite sides of the conduit, and
wherein each pressure member is plastic and formed as one-piece with an associated one of the actuator buttons.

26. A wearable infusion device comprising:
a base that contacts a patient's skin;
a reservoir arranged to contain a liquid medicant to be delivered beneath a patient's skin, the reservoir having an outlet through which the medicant flows;
a conduit communicating with the outlet of the reservoir the flexible conduit being configured to be compressed by at least one pressure member;

a pump comprising at least one pressure member that causes the medicant to flow down the conduit; and
a pair of actuator buttons coupled to the pump which, when concurrently pressed, cause the pump to cause the medicant to flow down the conduit.

27. The device of claim 26, wherein the actuator buttons are substantially opposed to each other.

28. The device of claim 26, further comprising a housing covering the base that encloses the reservoir, the conduit, and the pump, wherein the housing has an outer surface, and wherein each of the actuator buttons has an actuation surface separated from the housing outer surface to render the actuator buttons tactilely detectable.

29. The device of claim 28, wherein the actuation surfaces of the actuator buttons are recessed with respect to the housing outer surface.

30. The device of claim 26, further comprising a valve upstream from the pump that seals off the conduit from the reservoir as the pump causes the medicant to flow down the conduit, wherein the valve is closed responsive to the actuator buttons.

31. The device of claim 30, wherein the valve is closed when the actuator buttons are concurrently pressed.

32. The device of claim 26, wherein the pump is a mechanical pump.

33. The device of claim 26, further comprising a valve downstream from the pump.

34. The device of claim 33, wherein the valve downstream from the pump is a check valve.

35. The device of claim 33, wherein the valve downstream from the pump is a safety valve.

36. The device of claim 33, wherein the valve downstream from the pump is arranged to be actuated responsive to one of the actuator buttons being depressed.

37. The device of claim 33, wherein the valve downstream from the pump is arranged to be actuated into an open condition responsive to one of the actuator buttons being depressed.

38. A wearable infusion device comprising:
a base that contacts a patient's skin;
a reservoir arranged to contain a liquid medicant to be delivered beneath a patient's skin, the reservoir having an outlet through which the medicant flows;
a conduit communicating with the outlet of the reservoir the flexible conduit being configured to be compressed by at least one pressure member;
a pump comprising at least one pressure member that causes the medicant to flow down the conduit;
a housing covering the base that encloses the reservoir, the conduit, and the pump, wherein the housing has an outer surface, and
at least one actuator button coupled to the pump which, when pressed, causes the pump to cause the medicant to flow down the conduit, the at least one actuator button having an actuation surface separated from the housing outer surface to render the actuator button tactilely detectable.

39. The device of claim 38, wherein the actuation surface is recessed with respect to the housing outer surface.

* * * * *